(12) United States Patent
Bucs et al.

(10) Patent No.: US 10,502,675 B2
(45) Date of Patent: Dec. 10, 2019

(54) IN-LINE QUANTIFICATION AND CHARACTERIZATION OF MEMBRANE FOULING

(71) Applicant: KING ABDULLAH UNIVERSITY OF SCIENCE AND TECHNOLOGY, Thuwal (SA)

(72) Inventors: Szilard Bucs, Thuwal (SA); Sacco te Lintel Hekkert, Thuwal (SA); Marc Jaap Staal, Thuwal (SA); Johannes Vrouwenvelder, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 122 days.

(21) Appl. No.: 15/534,613

(22) PCT Filed: Dec. 10, 2015

(86) PCT No.: PCT/IB2015/002464
§ 371 (c)(1),
(2) Date: Jun. 9, 2017

(87) PCT Pub. No.: WO2016/092371
PCT Pub. Date: Jun. 16, 2016

(65) Prior Publication Data
US 2017/0363535 A1 Dec. 21, 2017

Related U.S. Application Data

(60) Provisional application No. 62/090,071, filed on Dec. 10, 2014.

(51) Int. Cl.
*G01N 17/00* (2006.01)
*B01D 61/12* (2006.01)
(Continued)

(52) U.S. Cl.
CPC .......... *G01N 17/008* (2013.01); *B01D 61/12* (2013.01); *B01D 65/08* (2013.01); *B01D 65/10* (2013.01);
(Continued)

(58) Field of Classification Search
CPC ...... G01N 17/008; G01N 21/94; B01D 61/12; B01D 65/08; B01D 65/10; B01D 2321/40
See application file for complete search history.

(56) References Cited

U.S. PATENT DOCUMENTS 6,161,435 A * 12/2000 Bond ............... B01D 61/12
210/785
8,210,042 B2 7/2012 Mickols et al.
(Continued)

FOREIGN PATENT DOCUMENTS

| NL | 1028474 | 3/2005 |
|---|---|---|
| WO | 2011153625 A2 | 12/2011 |
| WO | 2011163278 A2 | 12/2011 |

OTHER PUBLICATIONS

Chan, R., and V. Chen. "Characterization of protein fouling on membranes: opportunities and challenges." Journal of Membrane Science 242.1-2 (2004): 169-188 (Year: 2004).*
(Continued)

*Primary Examiner* — Dominic J Bologna
(74) *Attorney, Agent, or Firm* — Patent Portfolio Builders PLLC

(57) ABSTRACT

Methods of detecting, quantifying and/or characterizing the fouling of a device from a combination of pressure and spectroscopic data are provided. The device can be any device containing components susceptible to fouling. Components can include membranes, pipes, or reactors. Suitable devices include membrane devices, heat exchangers, and chemical or bio-reactors. Membrane devices can include, for example, microfiltration devices, ultrafiltration devices,
(Continued)

nanofiltration devices, reverse osmosis, forward osmosis, osmosis, reverse electrodialysis, electro-deionisation or membrane distillation devices. The methods can be applied to any type of membrane, including tubular, spiral, hollow fiber, flat sheet, and capillary membranes. The spectroscopic characterization can include measuring one or more of the absorption, fluorescence, or raman spectroscopic data of one or more foulants. The methods can allow for the early detection and/or characterization of fouling. The characterization can include determining the specific foulant(s) or type of foulant(s) present. The characterization of fouling can allow for the selection of an appropriate de-fouling method and timing.

18 Claims, 8 Drawing Sheets

(51) Int. Cl.
  *B01D 65/08* (2006.01)
  *B01D 65/10* (2006.01)
  *G01N 21/94* (2006.01)
(52) U.S. Cl.
  CPC ......... *G01N 21/94* (2013.01); *B01D 2321/40* (2013.01)

(56) References Cited

U.S. PATENT DOCUMENTS

| 8,348,499 | B2 | 1/2013 | Jons et al. | |
|---|---|---|---|---|
| 2008/0084565 | A1* | 4/2008 | Zribi | G01D 5/268 356/481 |
| 2009/0177412 | A1* | 7/2009 | Phattaranawik | B01D 61/025 702/35 |
| 2010/0012586 | A1* | 1/2010 | Angelescu | B01D 61/18 210/637 |
| 2013/0075331 | A1* | 3/2013 | Peiris | B01D 61/12 210/636 |
| 2013/0240440 | A1* | 9/2013 | Maung | B01D 61/12 210/636 |
| 2014/0000346 | A1* | 1/2014 | Hoek | B01D 61/025 73/38 |
| 2015/0021482 | A1* | 1/2015 | Muller | G01N 15/0205 250/341.1 |

OTHER PUBLICATIONS

International Search Report and Written Opinion of Application No. PCT/IB2015/002464 dated Apr. 18, 2016, 14 pages.
Daniel J. Miller, et al., Elsevier, SciVerse ScienceDirect, "Short-term adhesion and long-term biofouling testing of polydopamine and poly(ethylene glycol) surface modifications of membranes and feed spacers for biofouling control", Water Research 46 (2012) pp. 3737-3753, journal homepage: www.elsevier.com/locate/watres.
Communication pursuant to Article 94(3) EPC in corresponding/related EP Application No. 15828370.5, dated Oct. 14, 2019.

* cited by examiner

IN-LINE QUANTIFICATION AND CHARACTERIZATION OF MEMBRANE FOULING

CROSS-REFERENCE TO RELATED APPLICATION

This application is the National Stage of International Application No. PCT/IB2015/002464, filed 10 Dec. 2015, which claims the benefit of and priority to U.S. Provisional Patent Application No. 62/090,071 entitled "IN-LINE QUANTIFICATION AND CHARACTERIZATION OF MEMBRANE FOULING", filed on 10 Dec. 2014, all of which are expressly incorporated by reference as if fully set forth herein in their entirety.

BACKGROUND

Fouling is a common problem in water-based systems. Fouling can occur in a component in the system, such as in a heat exchange, a reactor or in a section of pipe or conduit in the system. Fouling can also occur in a component of a device in the system, such as a membrane in a filtration module. For example, fouling of filtration modules in high quality water production plants and industrial heat exchangers is a major operational problem in such systems. Membrane fouling can result in decreases in production (reduced water production, reduced heat transfer); increases in operational energy demands; costly system outages due to cleaning/de-fouling of the membrane; increased costs of system maintenance; and overall aging/wear on the systems.

Failure to timely clean components in water-based systems can result in higher cleaning costs (e.g. longer cleaning times, additional cleaning agents, use of more aggressive cleaning agents, etc.) and premature component replacement. For example, loss of operating time and increased costs associated with membrane cleaning and premature filtration module replacement along with reduced operating performance result in overall increased separation costs. Thus, it is important to carefully monitor fouling in order to optimize system performance, cleaning and component longevity.

Fouling of components in water-based systems is a physiochemical phenomenon that occurs when one or more of the components become coated or blocked by an accumulation of one or more various materials, foulants. The foulants can be from a variety of sources: inorganic, organic, colloidal, microbial, etc.; and each type of foulant can be most readily removed by different cleaning procedures. Identification of both the amount and the type of foulant can thus be important in selecting an appropriate cleaning treatment.

Filtration modules and heat exchangers are examples of closed non-transparent components usually operating under high pressure/high temperature. Direct measurements and monitoring systems to detect and determine the fouling type of closed components in operation are not available. These difficulties are especially true for spiral wound module configurations. Spiral wound membrane modules are a particularly important filtration technique for the production of high quality drinking water from seawater. Due to their spiral configuration, it is difficult to visually inspect the membrane surface without destroying or otherwise compromising the integrity of the module. Fouling detection and analysis in these modules are based on monitoring operational parameters like pressure drop along the modules, permeate production/heat transfer etc. When one or multiple parameters exceed a predefined threshold cleaning is applied. Indirect measures including permeate flow rates, permeate recovery ratios, operating pressures, feed temperatures and permeate quality can be influenced by factors unrelated to membrane fouling, such as concentration polarization.

Further, current systems are not sensitive enough to indicate fouling at an early stage and further do not provide sufficient information concerning the type of fouling that is needed to determine the fouling treatment method(s) needed. Typically determination of the type of fouling requires removal and opening of a component, and samples taken and analyzed in a laboratory.

SUMMARY

Methods of detecting, quantifying and/or characterizing fouling of one or more components in fluid-based systems are provided. In various aspects methods of detecting, quantifying and/or characterizing accumulation of one or more foulants in a component in a fluid-based system are provided. The methods can include: collecting fouling data of the component by irradiating the component with a light source and collecting data in the form of spectroscopic data from the component, or by collecting data including a pressure difference in the component, the pressure difference data representative of two or more time intervals or by collecting both the spectroscopic data and the pressure difference data; determining the presence of fouling or the degree of fouling of the component or both from the fouling data; and characterizing the type of fouling of the component from the fouling data. The fluid can be a liquid or gaseous substance containing a biological organic, inorganic or particular matter, or any combination thereof.

In any one or more aspects, the present methods of detecting and characterizing fouling can be applied to a number of different components in a fluid-based system. For example they can be applied to a microfiltration device, an ultrafiltration device, a nanofiltration device, a reverse osmosis device, a heat exchanger device, a forward osmosis device, an osmosis device, a reverse electrodialysis device, an electro-deionisation device, a membrane distillation device, or a section of a pipe, among any other components in a fluid-based system. The component can be or include a membrane selected from the group consisting of tubular, spiral, hollow fiber, flat sheet and capillary membranes.

The method can include characterizing the fouling of the component or test component, including the quantifying the fouling level and characterizing the identity of the foulant. The characterization can include characterizing more than one foulant or foulant level. The foulant can be an inorganic, organic, colloidal, or microbial foulant.

In various aspects the method can include providing a monitoring unit in-situ in the system, for example in-line with or in a line parallel to the component, wherein the monitoring unit includes one or more test components. The monitoring unit and/or test component(s) can be configured to mimic one or more components in the system. The fouling data can be collected from the monitoring unit and/or test component(s) and fouling of the component in the system determined and characterized as described in any one or more aspects herein.

In one or more embodiments a device is provided for detecting, quantifying and/or characterizing accumulation of one or more foulants in one or more components in a fluid-based system. In one or more aspects, the device can be a non-intrusive analytical sensor that provides for fouling detection. The device can include one or more monitoring units. The monitoring units allow for the interrogation of the one or more test components, in particular fouling of the test component(s), without the need for shutting down the device and especially without the need for shutting down the component(s) in the system to be monitored for fouling by the device. The monitoring unit can contain one or more test components designed to mimic the fouling of one or more components in the system. Mimicking the fouling of the component(s) in the system can include mimicking the presence of fouling, the amount of fouling, or the type(s) of foulants present in or on the component(s) in the system, or any one or more combinations thereof. The device can be any device in which fouling can occur. In one or more aspects the device is configured to be placed in-line, or in a line in parallel, with one or more components in the system to be monitored for fouling. The device can also include one or more pressure sensors, flow-rate sensors, light sources and/or spectroscopic sensors to obtain data from which fouling can be determined.

In any one or more aspects, the pressure difference can be a pressure drop across a component or across a test component over time. The pressure difference can be measured continuously and also semi-continuously such as, but not limited to, once every 10 seconds, 30 seconds, 10 minutes, 30 minutes, or one hour.

In any one or more aspects, the spectroscopic data can be absorption data reflectance data or luminescence data, or a combination thereof. The light source can include infrared light. The spectroscopic data can also be fluorescence data, luminescence data, Raman data, or Resonance Raman data, wherein the light source includes UV radiation.

Other methods, devices, features, and advantages of the present disclosure will be or become apparent to one with skill in the art upon examination of the following drawings and detailed description. It is intended that all such additional methods, devices, features, and advantages be included within this description, be within the scope of the present disclosure, and be protected by the accompanying claims.

BRIEF DESCRIPTION OF THE DRAWINGS

Many aspects of the disclosure can be better understood with reference to the following drawing. The components in the drawings are not necessarily to scale, emphasis instead being placed upon clearly illustrating the principles of the present disclosure. Moreover, in the drawing, like reference numerals designate corresponding parts throughout the several views.

FIG. 1 depicts an exemplary monitoring unit having a test membrane and a plurality of quartz windows.

FIGS. 2A and 2B depict data collected through windows 2 and 4 of one monitoring unit. FIGS. 2C and 2D depict data collected through windows 2 and 4 of a second monitoring unit.

DETAILED DESCRIPTION

Figure 1A:
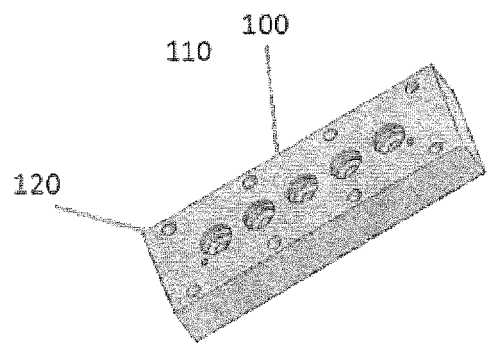
FIG. 1A depicts a perspective view of an upper section of the monitoring unit.
Figure 1C:
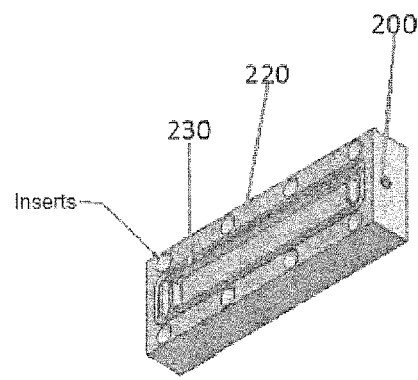
FIG. 1C depicts a perspective view of a lower section of the monitoring unit.
Figure 1B:
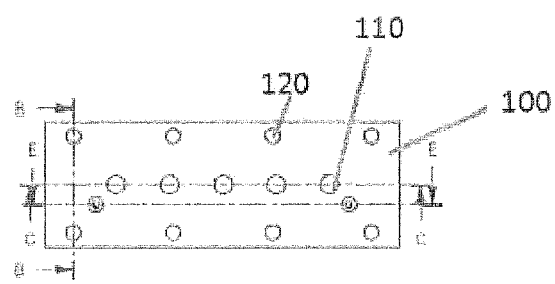
FIG. 1B depicts a plan view of the inside surface of the upper section of FIG. 1A.
Figure 1D:
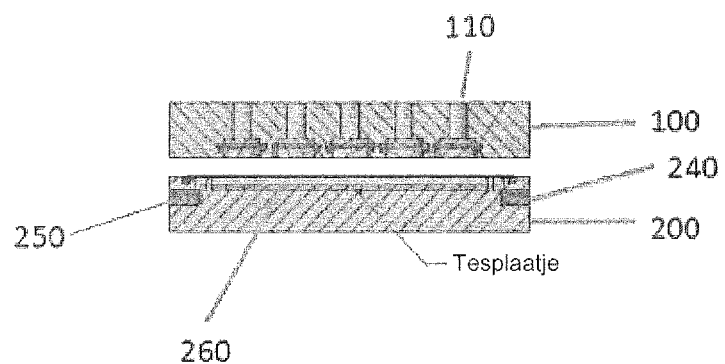
FIG. 1D depicts a cross-section of the upper and lower sections of FIGS. 1A-1C taken along line E-E of FIG. 1B.

Described below are various embodiments of the present methods and device for detection, quantification and/or characterization of fouling of a component or a test component in a water-based system. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Before the present disclosure is described in greater detail, it is to be understood this disclosure is for illustrative purposes only. The terminology used is to describe particular embodiments, and is not intended to be limiting.

I. Methods of Characterizing Fouling

Methods of detecting the presence and/or quantifying the extent of fouling of a component in a fluid-based system are provided. The fluid can be a liquid or a gaseous substance containing biological, organic, inorganic or particulate matter or any combination thereof. A variety of components in fluid-based systems, for example in water treatment devices, industrial reactors, or heat exchangers, can exhibit fouling. The components can be membrane devices such as micro-filtration or nano-filtration devices, heat exchangers, or reactors. The fouling can include the accumulation of one or more foulants as described below on or in the component. For example, the fouling can include the accumulation of one or more foulants on or in a membrane, on the interior surface of a pipe, or on the interior of a reactor.

The methods also allow for the characterization of fouling of components in the systems. The methods are non-intrusive or minimally intrusive. The methods can be performed in-line, or in a line in parallel with the components, under operational conditions such as high temperature or pressure, with no system outage, without the removal of the membrane, or a combination thereof.

The methods can include collecting fouling data that detects, quantifies and/or characterizes the fouling of the components. The fouling data can include pressure difference, flow rate, or spectroscopic data of a foulant, or one or more combinations thereof, each of which are described in more detail below. Fouling can be determined from the data collected. Not only can the presence of fouling be determined from the data, but also the amount of fouling quantified and/or the type of fouling characterized.

In some aspects, some or all of the method steps described herein can be automated. As used herein, the term "automated" means the steps can be performed without continuous supervision or intervention by an operator, for example the steps can be computer controlled. Steps that are performed without any automation, but are performed directly by an operator, are referred to herein as "manual" steps. The term "semi-automated" is used herein to refer to steps that can be performed in an automated fashion aside from periodic supervision or intervention. In some embodiments, the various steps of collecting the fouling data can be automated or semi-automated. The steps of populating the fouling data in a database, comparing the fouling data to the data in a database, or characterizing the fouling, including characterizing the amount of fouling and/or characterizing the foulants, can be automated or semi-automated. In some embodiments the entire method can be performed in an automated or semi-automated manner. In other embodiments one or more of the steps may be manual.

Methods of Measuring Pressure Difference

The fouling data can include pressure difference data. The methods can include measuring a pressure difference in one or more components in the system. Methods of measuring pressure and pressure differences are known to those skilled in the art. The pressure difference can be measured directly using a differential pressure sensor. The pressure difference can be measured as a difference between two or more pressure measurements or readings. The pressure measurements can be absolute pressure measurements (relative to vacuum), gauge pressure measurements (relative to atmospheric pressure), or a differential pressure measurement relative to a fixed reference pressure.

The pressure difference can be a pressure drop across the component or across a module containing one or more components. For example, the pressure difference can be a pressure drop across a membrane in a module or component. The pressure difference can be a pressure drop across a test component or across a monitoring unit containing a test component. Test components include, for example test membranes, test pipes, or test reactors, that are designed to mimic the fouling of the component to be monitored in the system. For example, a test membrane can be designed to mimic the fouling of a membrane in a component in the system.

The pressure difference can be a difference in pressure over time, e.g. the pressure difference can be a difference in pressure between a reference or first time and a later or second time. In some embodiments the reference time is at a time where there is little or no fouling of the component.

The pressure difference can be determined from a continuous measurement of pressure or from two or more pressure measurements taken at discrete times, for example once every 10 seconds, 30 seconds, minute, 10 minutes, 30 minutes, or hour. The pressure difference can be measured in units of pascal (Pa), pounds per square inch (psi), millimeters mercury (mmHg), or inches of water (in. W. C.). The pressure can be a dynamic pressure or a total pressure, i.e. a combination of static and dynamic pressure.

Methods of Measuring Flow Rate

The fouling data can include flow rate data. The methods can include measuring a flow rate. Methods of measuring flow rate are known in the art. The flow rate can be the rate of flow of a fluid through one or more components in the system or through a module containing one or more of the components. The flow rate can be through a test or device component or through a monitoring unit containing a test component. The flow can be measured in any unit of volume per unit of time such as cubic meters per second ($m^3\ s^{-1}$) or cubic feet per second ($ft^3\ s^{-1}$). The flow rate can be measured continuously or at discrete times once every 10 seconds, 30 seconds, minute, 10 minutes, 30 minutes, or hour.

Methods of Spectroscopic Characterization of Foulants

The fouling data can include spectroscopic data of one or more foulants. The methods can include collecting spectroscopic data of a foulant in or on a component. The foulant can be on or in any part of a component in the system. In some embodiments the foulant is in or on a test component, for instance a test membrane, a test pipe, or a test reactor, optionally in a monitoring unit. Methods of spectroscopic characterization and identification of materials are generally known.

The spectroscopic methods can include measuring absorption, emission, or reflection of light or a combination thereof. The emitted, absorbed, and/or reflected radiation can be visible, UV, near UV, deep UV, IR, NIR, SWIR, MWIR, LWIR, violet, indigo, blue, cyan, green, yellow, orange, red, or a combination thereof.

The spectroscopic methods will generally include irradiating the foulant in or on the component with light from a light source. The light from the light source can be broadband or monochromatic. The light from the light source can be visible, UV, near UV, deep UV, IR, NIR, SWIR, MWIR, LWIR, violet, indigo, blue, cyan, green, yellow, orange, red, or a combination thereof.

The spectroscopic data can include absorption data of one or more foulants. Methods of collecting absorption data are generally known. The light can be visible, typically violet, indigo, blue, cyan, or green; ultraviolet, typically near UV; or a combination thereof. The foulant(s) will absorb specific wavelengths of light that are indicative of the specific foulant or type of foulant.

The spectroscopic data can include luminescence data of one or more foulants. The methods can include collecting luminescence data of one or more foulants. Collecting luminescence data can include irradiating the foulant with light of a certain wavelength and intensity followed by measuring the wavelength and intensity of light emitted by the foulant(s). The light can be visible, typically violet, indigo, blue, cyan, or green; ultraviolet, typically near UV; or a combination thereof. The intensity of the emitted light can be correlated with the amount of the specific foulant that is on the component.

Each foulant or type of foulant will emit at a specific wavelength (emission wavelength) of light when irradiated with a specific wavelength (excitation wavelength) of light. The emission wavelength will be at a longer wavelength (lower energy) than the excitation wavelength. This combination of excitation wavelength and emission wavelength can be used to identify the foulant or type of foulant. The spectroscopic data can include an Excitation-Emission Matrix (EEM). The EEM, as the term is used herein, is defined as the luminescent emission intensity of fluorescent substances as a function of both excitation and emission wavelength. This can include a full spectrum over a given range of wavelengths or a subset of a single or multiple excitation/emission pairs. The EEM can include more than one specific excitation-emission wavelength pair, e.g., at least at 2, 3, 4, 5, 6, 7, 8, 9, 10, 15, 20, 25, 50, or more specific excitation-emission wavelength pairs.

The spectroscopic data can include Raman or Resonance Raman data. Raman spectroscopy is the measurement of the wavelength and intensity of inelastically scattered light from the foulant. The incident/source light can be shifted to lower energy (longer wavelength), which is called "Stokes shift", or to higher energy (lower wavelength), which is called "anti-Stokes shift". Raman spectroscopy requires little to no sample preparation and requires no reagent additions. Raman spectroscopy can readily be used in aqueous systems since the water molecule has very weak Raman activity. Raman spectroscopy can include irradiating the foulant with a high intensity light source, e.g. a laser, typically in the visible or NIR region. The intensity of a Raman shift line is proportional to the fourth power of the excitation source frequency. Therefore, for example, using a light source in the red region produces relatively low intensity lines. A shorter wavelength (higher frequency) excitation source in the green or blue region can be obtained by using, for example, a Nd:YAG laser at 532 nm. The higher excitation frequency will increase the intensity of the Raman shift line. The problem with doing this, however, is that many organic compounds including many of those found in wastewater, exhibit strong fluorescence of blue and green wavelengths making it challenging to obtain good signal-to-noise ratios. Going to even shorter wavelengths into the UV, near UV, and deep UV region will further increase the intensity of the Raman shifts due to the effect of the higher frequency excitation. This also avoids the potential interference from fluorescence since condensed phase species typically show no fluorescence below 260 nm. Many foulants can exhibit UV absorption making it possible to take advantage of the resonance Raman effect. Resonance Raman scattering requires excitation within an electronic absorption band and results in a large increase of scattering. The resonance Raman scattering can be up to about $10^8$ times that of "normal" Raman scattering Foulants Typical "foulants" or "membrane foulants" can include colloidal suspended solids such as clays and silt, metal hydroxides such as iron hydroxide originating from corrosion of steel piping and tanks, naturally occurring organic matter (NOM) including humic substances, soluble organic compounds and insoluble "oil and grease" which are typically present in industrial effluents and "bio-foulants". The "bio-foulants" can be "aerobic" or "anaerobic" bio-mass which form due to the bio-degradation of organic compounds in the water in the presence, or absence, of oxygen, respectively. While "membrane foulants" affect all types of membranes, including reverse osmosis membranes (RO), forward osmosis membranes, osmosis membranes, nanofiltration membranes (NF), ultrafiltration membranes (UF) and microfiltration membranes (MF), scale formation typically occurs in RO and NF membranes only as a consequence of "concentration" of "sparingly or partially soluble" inorganic scale compounds including calcium carbonate, silica and calcium sulphate when these compounds are rejected by these "tight" membranes. The foulants can be in or on any component in the system, for example in or on a membrane, a pipe, or a reactor in the device or in or on a monitoring unit and/or a test component.

Methods of Using Fouling Data

Characterization and/or identification of the foulant need not involve identification of an exact species. Characterization can encompass the broad categorization or classification of foulant particles as well as the actual identification of a single foulant species. In some embodiments, the characterization and/or identification includes identification of the specific species of one or more foulants. In some embodiments, the characterization and/or classification includes identification of a specific classification of the foulant. If a biological foulant (bio-fouling), the identification can include determining to which family, genus, species, and/or strain the foulant belongs to.

Characterization and/or identification can include determining the amount of specific family or genus classes of foulants on the component in the device. The characterization and/or identification can include sufficient information about the type and amounts of foulants to select the most effective de-fouling method from a set of de-fouling methods. The characterization and/or identification can include sufficient information about the type and amounts of foulants to select the optimal time to perform a specific de-fouling method, for example to reduce wear on a membrane or other component, to prevent irreversible fouling of a membrane, to minimize the overall production costs of de-fouling, or a combination thereof.

The de-fouling methods can include physical, chemical, or physio-chemical de-fouling methods. Physical cleaning methods use mechanical forces to dislodge and remove foulants, including sponge ball cleaning, forward and reverse flushing, backwashing, air flushing, and $CO_2$ back permeation for example. The de-fouling methods can include the use of chemicals or gases.

Fouling can be physically reversible fouling which can be totally or almost totally eliminated by physical cleaning, and physically irreversible fouling that is largely not removed by physical cleaning. Chemical cleaning should typically be limited to a minimum frequency since repeated chemical cleaning may negatively affect membrane life. The choice of the cleaning agent can be important to maximize membrane lifetime.

II. Devices

In one or more embodiments, a device is provided for detecting, quantifying and/or characterizing fouling of a component in a water-based system. The device can be any device in which fouling can occur. The device can include one or more monitoring units for monitoring the fouling of one or more components of the system. The monitoring units allow for the interrogation of the one or more test components, in particular fouling of the test component(s), without the need for shutting down the device and especially without the need for shutting down the component(s) in the system to be monitored for fouling by the device. The monitoring unit can contain one or more fouling components or test components designed to mimic the fouling of one or more components in the system. Mimicking the fouling of the component(s) in the system can include mimicking the presence of fouling, mimicking the amount of fouling, or mimicking the type(s) of foulants present in or on the component(s) in the system, or any one or more combinations thereof. The one or more monitoring units can include one, two, three, four, or more test components. The monitoring unit can contain one or more observation windows, e.g., quartz or glass windows, that allow for irradiating the test component(s) with light and measuring the absorbed and/or emitted light. In one or more aspects the device is configured to be placed in-line, or in a line in parallel, with one or more components in the system to be monitored for fouling. The device can also include one or more pressure sensors, flow-rate sensors, light sources and/or spectroscopic sensors, as described herein, to obtain fouling data from which fouling can be determined.

Fouling Components

The device, in particular, the one or more monitoring units, will generally include one or more test components that are susceptible to fouling. For example, the device can include a purification device, a filtration device, a size-exclusion device, a microfiltration device, an ultrafiltration device, a nanofiltration device, a reverse osmosis device, a forward osmosis device, an osmosis device, a reverse electrodialysis device, an electro-deionisation device, a membrane distillation device, a membrane, a pipe or a section of a pipe, and/or a reactor that, or any combinations thereof, that are susceptible to and can exhibit fouling.

The device can contain one or more membranes. For example, the device can contain one, two, three, four, or more membranes. The membranes can be the same or different types of membrane configurations. The membranes can be arranged in a parallel or serial arrangement.

Most membranes can be classified in five basic configurations. Each can be configured differently, both in packaging and in the types of materials used. The membrane can be a tubular membrane, a spiral membrane, a hollow fiber membrane, a flat sheet, or a capillary membrane.

A spiral membrane is typically made from layers of flat-sheet membranes and feed separators wrapped around a hollow core. Solutions enter one end of the membrane, flowing under pressure through the membrane into permeate channels, spiral to the central core, and exit as permeate. This configuration offers one of the higher membrane-packing areas with the smallest footprint.

The device can contain one or more pipes. The term "pipe" is used broadly herein to cover any elongated hollow member defined by an outer wall designed for transporting liquid and/or gaseous materials (fluid materials) therein. The outer wall of the pipe can be made of any suitable material and can have one or more protective coatings on the interior and/or the exterior surface. The pipe can have any shape suitable for the space in which the fluid must be distributed, such as parallelepiped, cylinder, cone, torus, etc.

The device can contain one or more reactors. The method can be applied to any reactor having a tendency of fouling. The reactor can be a chemical reactor for carrying out the reaction of one or more chemicals. The chemical reactor can be a polymerization reactor. U.S. 2010/0206334 describes fouling of polymerization reactors, specifically oligomerisation reactors for the oligomerisation of ethylene. Chemical reactors can include, for example, continuous stirred-tank reactors or plug flow reactors. The reactor can be a biological reactor or "bio-reactor". For example, a fermentor is a reactor designed for the cultivation of microorganisms. The environment in the vessel is closely controlled to enable the proper expression of biochemical reactions for the production of the desired by-product.

Pressure Sensors

The device can include one or more pressure sensors. The pressure sensor(s) are configured to measure pressure in the device and to provide pressure data from which a pressure difference in the device can be determined and noted, as described herein. The term pressure sensor describes all means, which are capable to measure a hydrostatic or pneumatic pressure or a force applied to the sensor. Pressure sensors are known to the skilled artisan. The pressure sensor may use the piezo-electric effect, the measurement of strain or stress of an elastic material or other parameter which vary under the influence of the pressure.

Flow-Rate Sensors

The device can include one or more flow sensors. The flow rate sensor(s) are configured to provide flow rate data of fluid flow through the device from which a flow rate difference in the device can be determined and noted, as described herein. Any suitable flow sensor can be used, such as a volumetric flow sensor or mass flow sensor, which is in fluid connection with the appropriate part of the device. Examples of flow sensor include magnetic flow sensor and paddle-type flow sensor. The signals generated by the flow sensor may be analog or digital.

Light Sources and Spectroscopic Sensors

The device can include one or more light sources and/or spectroscopic sensors for the optical interrogation of fouling in the device, in particular of the one or more test components in the monitoring unit of the device. The one or more light sources and/or spectroscopic sensors are configured to provide spectroscopic data, as further described herein. The spectroscopic methods for the optical interrogation can generally include irradiating the foulant on the one or more test components with a light source and detecting one or more spectroscopic data of the foulant. The light source can be a broadband light source, a monochromatic light source, or a combination thereof. There are a large variety of broadband or monochromatic sources to choose from, such as: incandescent, LED's, super luminescent diodes, lasers (fixed and tunable, diode, SS, gas), gas discharge lamps (line and continuum), with or without filters. Wavelength scanning is usually accomplished by coupling the sources with filter wheels, scanning monochrometers or acousto-optical tunable filters, or in the case of a laser source by using a tunable diode laser. The light sources can be characterized by the region of the electromagnetic spectrum of the wavelength(s) the light source produces. The light can be visible, typically violet, indigo, blue, cyan, or green; ultraviolet, typically near UV or UV; or a combination thereof.

Programming Logic

The device can include programming logic and conventional hardware for executing the programming logic. The hardware can include, for example, a processing unit and memory for storing and processing the aforementioned data, all of which are known and available to one skilled in the art. The programming logic can be configured to receive the fouling data and determine from the fouling data a detection of the presence of fouling, a quantification of the amount of fouling and/or a characterization of the type of fouling of the one or more components in the system.

In one or more aspects the device can be a non-intrusive in-situ analytical sensor that allows detection of fouling and/or the degree of fouling and characterization of different types of fouling by the use of non-intrusive spectral analysis of the fouling material in combination with pressure drop measurements. The device can be constructed in such a way that it can withstand pressure up to 70 bar, allowing for installation in current filtration based water production plants (spiral wound membrane systems) to do online detection and characterization of fouling types under operational conditions.

In one or more aspects the internal conditions inside the device can mimic the hydrodynamic conditions of one or more components in the system. A non-limiting example of one type of such components can be filters, for example spiral wound filters, which present in the system to be monitored and which can be connected parallel to the device. This will result in similar fouling conditions in the device as in regular filters and therefore become indicative for the amount of fouling in the real filters. The device can have windows that allow both absorption and fluorescence measurements. Absorption patterns can be indicative for different types of precipitation, organic as well as inorganic and can be used to determine different fractions in the fouled layer. In addition, several components of fouling material are auto fluorescent and can be used as indicator(s) to identify the nature of the type of fouling. One component that can be indicative for biological growth is the presence of tryptophan, which can be quantified by measuring the emitted light at 350 nm after excitation at 280 nm. Additionally the pressure drop can be monitored to measure the fouling level or intensity as an additional analytical parameter. A database of fouling types can be developed based on these parameters. The device combined with the database can define the fouling rate and type.

Thus, In one or more aspects, the device can include: 1) a monitoring unit including one or more test components for mimicking fouling in one or more components in the system to be monitored; 2) a flow sensor, for example a flow cell, that can mimic fluid flow through the monitored system (filtration module/heat exchanger), and can operate under high pressure to have similar hydrodynamic condition as in the monitored component(s) in the system; and 3) a spectroscopic sensor. The fouling monitoring unit can be, in whole or in part be transparent (glass and quartz windows) to allow in situ spectroscopic measurements. The spectroscopic sensor can include different excitation sources (for example, 280 nm, broad spectrum and 542,672 and 785) to excite fouling material. Analysis of the fouling material can be done based on respectively fluorescence, luminescence, reflection and Raman shifts, allowing the quantification of different fractions in the fouling material. In one or more aspects, the device can include one or more of the other aforementioned sensors. For example, the overall quantification of the fouling material can be done with a differential pressure sensor and a flow rate monitor can be included to measure operational performance decline.

FIG. 1 depicts an exemplary monitoring unit of the present disclosure. The monitoring unit includes an upper section or plate 100 (FIGS. 1A and 1B) and a lower section or plate 200 (FIG. 1C). In FIG. 1D the upper plate 100 is depicted in position above lower plate 200. The monitoring unit contains a test component 260, for example a test membrane, fitting into an opening in the lower section or plate 200 having a recess 230 for receiving the test component 260. The test component 260 is sandwiched between the lower plate 200 and the upper section or plate 100 and within the recess 230 of the lower plate 200. One or more light sources and/or spectroscopic sensors (not shown) can be combined or coupled with the monitoring unit. The upper plate 100 includes a plurality of quartz windows 110 for irradiating the test component 260 with light from the one or more light sources and measuring the absorbed and/or emitted light by the one or more spectroscopic sensors. The monitoring unit includes an inlet port 240 and outlet port 250 for allowing the fluid to move into and out of the monitoring unit and through the test membrane or test plate 260. A pressure sensor and/or a flow sensor (not shown) can be combined or coupled with the monitoring unit to measure pressure in the monitoring unit and/or the flow of fluid through the unit, respectively. The monitoring unit can be designed such that the fouling of the test component 260 mimics the fouling of a component in the system to be monitored for fouling.

III. Definitions

The terms "purification" and "filtration", as used interchangeably herein, refer generally to a process of removing one or more contaminating species, for example and not limitation, excess salt (e.g. bisulfite), from a bisulfite-treated nucleic acid sample. Likewise, purified product or purified nucleic acid refer to the resultant products of such purification.

The term "current exchange", as used herein, refers generally to a process of transferring some physical or chemical property from one flowing fluid (liquid or gas) to another flowing fluid (liquid or gas). The property can be heat ("heat exchanger") or specific chemical species. The heat exchanger can include a thermoconductive membrane, i.e. a membrane that allows heat transfer between a first liquid or gas on one side of the membrane and a second liquid or gas on the opposite side of the membrane. The thermoconductive membranes can be made from any thermally conductive material such as ceramics, metals, and thermally conductive polymers.

The term "size-exclusion", when used herein to refer to purification or filtration devices, refers to devices capable of separating materials on the basis of their size. One non-limiting exemplary class of such devices is the membrane filtration-type class, wherein sample components are separated on the basis of molecular weight through a membrane that allows small molecules to pass through more rapidly than larger molecules. Typically, membrane filtration-type devices are characterized by a molecular weight cutoff that represents an upper limit of the molecular size of molecules that are able to pass through the matrix. Typically, a sample solution or reaction mixture is forced through the molecular weight separation matrix by application of centrifugal force (by centrifugation) or positive pressure (e.g., application of gaseous pressure or application of a piston above the solution or reaction mixture).

The term "nominal pore size (NPS)", as used herein, refers to the minimum size of particles that will be retained by membrane. Particles with a diameter greater than the NPS will be retained to at least 75%, 80%, 85%, 90%, or 95% by the membrane.

The term "nominal molecular weight limit (NMWL)", as used herein, refers to the exclusion limit of a size-exclusion membrane. The NMWL is related to the pore size and is defined as the minimum molecular weight of a globular or spherical molecule that is retained to at least 75%, 80%, 85%, 90%, or 95% by the membrane.

The term "microfiltration", as used herein, refers to a size-exclusion filtration that removes particles such as microorganisms and suspended particles having micrometer dimensions. The microfiltration membranes are specially designed to prevent particles such as, sediment, algae, protozoa or large bacteria from passing through the membrane. More microscopic, atomic or ionic materials such as water ($H_2O$), monovalent species such as Sodium ($Na^+$) or Chloride ($Cl^-$) ions, dissolved or natural organic matter, and small colloids and viruses will still be able to pass through the filter. The typical particle size used for microfiltration ranges from about 0.1-100 µm, 0.1-50 µm, 0.5-20 µm, or 0.5-10 µm. Microfiltration membranes typically have a NPS of greater than about 0.1, 0.2, 0.3, 0.4, 0.5, or 1.0 µm. Microfiltration membranes typically have a NMWL of greater than about 3,000, 4,000, 5,000, 6,000, 8,000, or 10,000 kDa. Microfiltration devices are typically operated at low to moderate pressures about 0.1-4 bar, 0.1-3 bar, 0.1-2 bar, 0.5-2 bar, 1-2 bar. Microfiltration membranes can be organic or inorganic. Organic membranes can include a various polymers including cellulose acetate (CA), polysulfone, polyvinylidene fluoride, polyethersulfone and polyamide. Inorganic membranes can contain sintered metal or porous alumina.

The term "ultrafiltration", as used herein, refers to a size-exclusion filtration that removes particles such as emulsified oils, metal hydroxides, colloids, emulsions, dispersed material, suspended solids, and other large molecular weight materials. Ultrafiltration can be used for the clarification of solutions containing suspended solids, bacteria, and high concentrations of macromolecules, including oil and water, fruit juice, milk and whey, electrospray paints, pharmaceuticals, poly-vinyl alcohol and indigo, potable water, and tertiary wastewater. The typical particle size used for ultrafiltration ranges from about 1-500 nm, 1-300 nm, 2-300 nm, 2-200 nm, or 2-100 nm. Ultrafiltration membranes typically have a NPS of greater than about 1, 1.5, 2, 2.5, 3, 4, or 5 nm. Ultrafiltration membranes typically have a NMWL of greater than about 5 kDa, 10 kDa, 50 kDa, 100 kDa, 200 kDa, 300 kDam, or 500 kDa. Ultrafiltration devices are typically operated at higher pressures about 1-20 bar, 1-15 bar, 1-10 bar, 2-10 bar, or 2-5 bar. Ultrafiltration membranes can be organic or inorganic. Organic membranes can include a various polymers including cellulose acetate (CA), polysulfone, polyvinylidene fluoride, polyethersulfone and polyamide. Inorganic membranes can contain porous ceramics.

The term "nanofiltration", as used herein, refers to a size-exclusion filtration that removes particles such as small organic species, viruses, and divalent ionic species. Small monovalent ions such as $Na^+$ and $Cl^-$ are not typically retained by nanofiltration. Nanofiltration membranes have become increasingly used for water purification. The typical particle size used for nanofiltration ranges from about 1-10 nm, 1-8 nm, 1-6 nm, 1-5 nm, or 1-4 nm. Nanofiltration membranes typically have a NPS of greater than about 0.5, 1.0, 1.2, 1.4, 1.6, 1.8, 2.0, 3.5, 4.0, or 5.0 nm. Nanofiltration membranes typically have a NMWL of greater than about 10, 50, 100, 150, 200, 300, 400, or 500 Da. Nanofiltration devices are typically operated at very high pressures about 2-70 bar, 2-60 bar, 2-50 bar, 2-30 bar, or 3-20 bar. Nanofiltration membranes can be organic or inorganic.

The term "reverse osmosis membrane", as used herein, refers to a dense semi-permeable membrane used for separation of salts (monovalent and divalent) and small molecules from water and certain other liquids. The reverse osmosis membrane is technically not a size-exclusion membrane but is based on the preferential diffusion of water or other small species through the membrane when subjected to very high pressures, e.g. above the osmotic pressure. Typical pressures can include 10-200 bar, 20-200 bar, 30-200 bar, 30-150 bar, 30-100 bar, or 30-80 bar. Typical pore diameters in reverse osmosis membranes are less than 1.5 nm, less than 1.2, less than 1.0 nm, or less than 0.8 nm.

When referring to radiation, as used herein, the term "visible" refers to radiation having a wavelength of about 300-800 nm, about 325-750 nm, about 350-740 nm, or about 370-720 nm; the term "ultraviolet" or "UV" refers to radiation having a wavelength of about 150-450 nm, about 170-400 nm, about 190-350 nm, or about 200-300 nm; and the term "infrared" or "IR" refers to radiation having a wavelength of about 0.7-1,000 μm, about 0.7-50 μm, about 0.74-14 μm, about 0.75-8 μm, or about 0.75-5 μm. The radiation can be described herein as "near ultraviolet" or "near UV" when the wavelength of the radiation is about 290-430 nm, about 300-400 nm, about 310-395 nm, or about 320-380 nm. The radiation can be described herein as "deep ultraviolet" or "deep UV" when the wavelength of the radiation is about 150-320 nm, about 185-310 nm, or about 200-300 nm. The radiation can be described herein as "violet" if it has a wavelength of about 300-450 nm, about 325-440 nm, about 350-430 nm, or about 360-420 nm; as "indigo" if it has a wavelength of about 400-480 nm, about 420-460 nm, about 430-450 nm, or about 440 nm; as "blue" if it has a wavelength of about 430-520 nm, about 440-510 nm, about 450-500 nm, or about 460-490 nm; as "cyan" if it has a wavelength of about 480-540 nm, about 490-530 nm, about 500-520 nm, or about 501 nm; as "green" if it has a wavelength of about 500-600 nm, about 510-580 nm, about 520-565 nm, or about 540-550 nm; as "yellow" if it has a wavelength of about 540-610 nm, about 550-600 nm, about 564-590 nm, or about 589 nm; as "orange" if it has a wavelength of about 570-650 nm, about 580-640 nm, about 590-625 nm, or about 593 nm; and as "red" if it has a wavelength of about 600-800 nm, about 610-780 nm, about 625-740 nm, or about 650-720 nm. The radiation can be described herein as "near infrared" or "NIR" if it has a wavelength of about 700-3,000 nm, about 740-1,400 nm, or about 750-1,000 nm; as "short-wave infrared" or "SWIR" if it has a wavelength of about 850-2,000 nm, about 900-1,700 nm, or about 1,000-1,400 nm; as "medium-wave infrared" or "MWIR" if it has a wavelength of about 2-8 μm, about 3-5 μm, or about 3.5-4.5 μm; and as "long-wave infrared" or "LWIR" if it has a wavelength of about 7-14 μm, about 8-12 μm, or about 9-10 μm.

Where a range of values is provided, it is understood that each intervening value, to the tenth of the unit of the lower limit unless the context dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both are also included in the disclosure.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

All publications and patents cited in this specification are incorporated by reference as if each individual publication or patent were specifically and individually indicated to be incorporated by reference and are incorporated by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could differ from the actual publication dates that may need to be independently confirmed.

As will be apparent to those of skill in the art upon reading this disclosure, each of the individual embodiments described and illustrated has discrete components and features which may be readily separated from or combined with the features of any of the other several embodiments without departing from the scope or spirit of the present disclosure. Any recited method can be carried out in the order of events recited or in any other order logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

Embodiments of the present disclosure will employ, unless otherwise indicated, techniques of molecular biology, microbiology, nanotechnology, organic chemistry, biochemistry, botany which are within the skill of the art. Such techniques are explained fully in the literature.

Examples

Now having described the embodiments of the present disclosure the following Examples describe some additional embodiments of the present disclosure. While embodiments of the present disclosure are described to follow examples and the corresponding text and figures, there is no intent to limit embodiments of the present disclosure to this description. The intent is to cover all alternatives, modifications, and equivalents within the spirit and scope of embodiments of the present disclosure.

The monitoring unit of FIG. 1 was used to test a sample of surface water from The Netherlands for fouling over a period of seventeen (17) days. The tests were run at 18° C. at 1 atm. The sample was irradiated with a light source and spectroscopic data was collected from the irradiation of the sample. The spectroscopic data included both luminescent spectra and absorption spectra. In addition a pressure difference was monitored over the period of the test.

For the absorption measurements we used a broad spectrum light source, while for the luminescence spectra a narrow band LED 285 nm excitation source was used. Luminescent spectra were made using windows 2 and 4 (FIG. 2) which had crystal glass windows more suitable for obtaining luminescent spectra. Absorption spectra were made using windows 1-4 of the monitoring unit. Window 3 (FIG. 3(a)) depicts a representative example of the absorption spectra. It should be understood, however, that any one or more of the windows in the monitoring unit may be used to obtain the luminescent spectra or the absorption spectra or both.

Figure 2A:
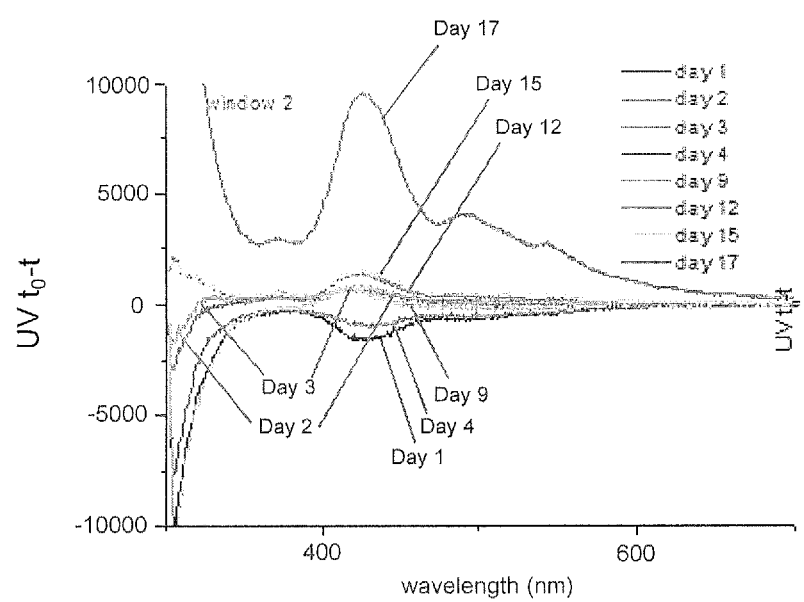
FIGS. 2A-2D depict spectroscopic data, in particular luminescent spectra, collected using the monitoring unit of FIG. 1 showing an increase in peak intensity at 430 nm at 285 nm excitation with biomass increase in the developed monitoring unit over time.
Figure 2B:
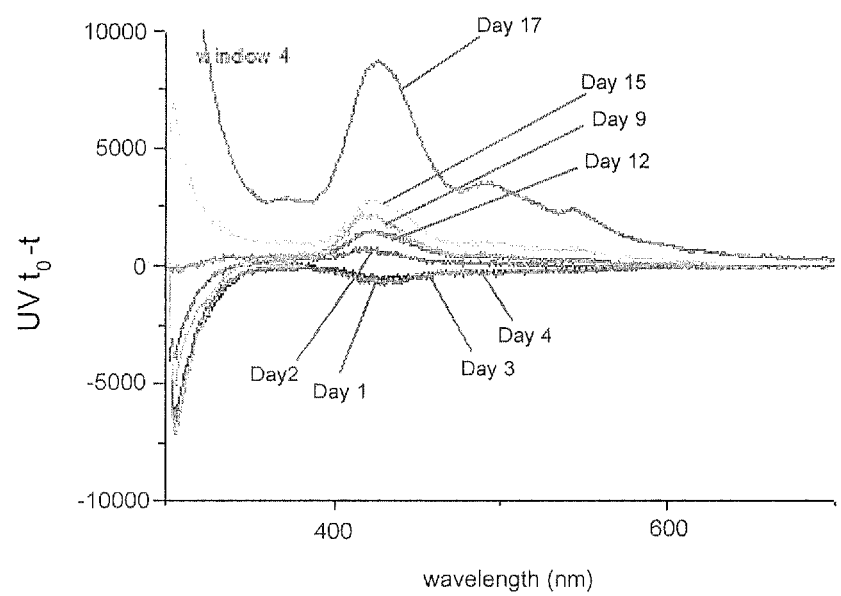
Figure 2C:
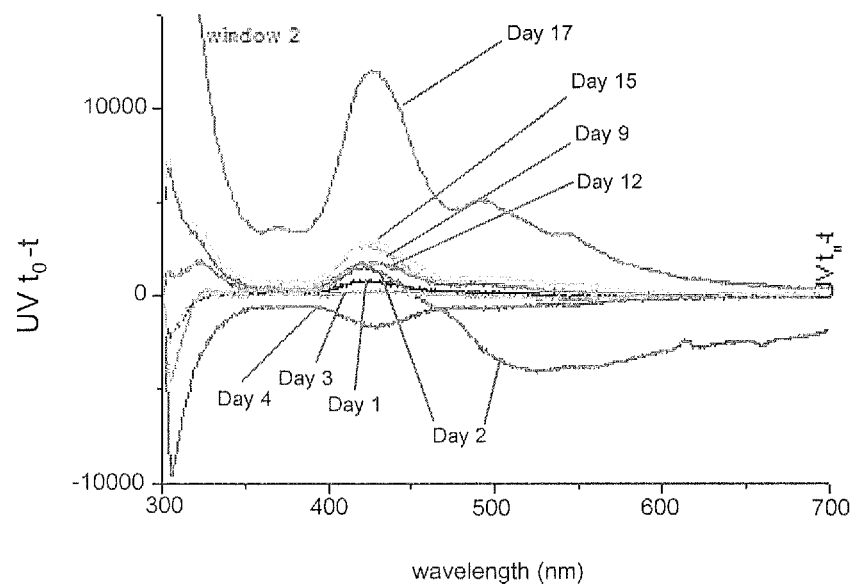
Figure 2D:
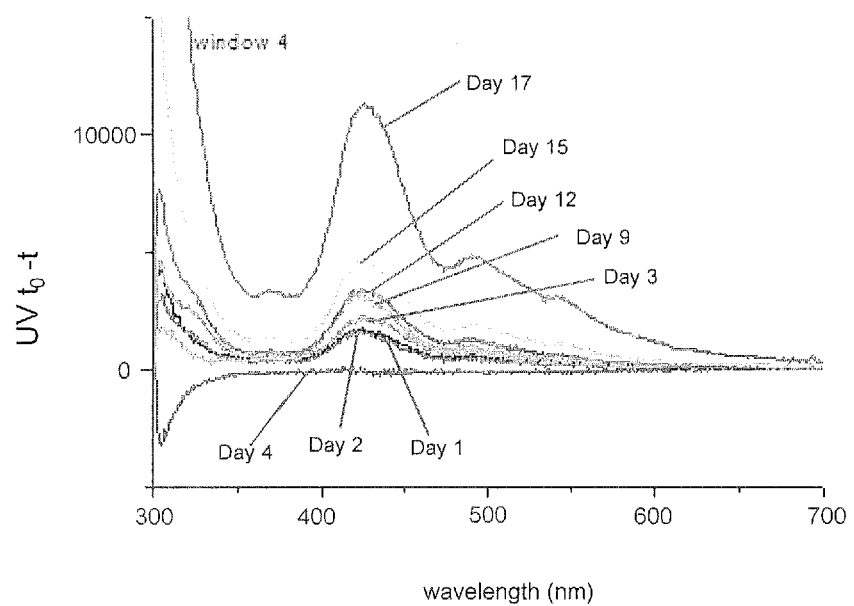

FIGS. 2A and 2B depict spectroscopic data, in particular luminescent spectra, collected through windows 2 and 4 of the unit. FIGS. 2C and 2D depict data collected through windows 2 and 4 of a second monitoring unit. Emission spectra at 350 nm and 420 nm indicates the presence of biomass and organic material. The emission peak at 560 nm indicates organic deposition. As can be seen, there is little difference between the spectra obtained from the different windows, showing that representative spectra can be obtained from either or both windows or even from any of the windows.

Figure 3A:
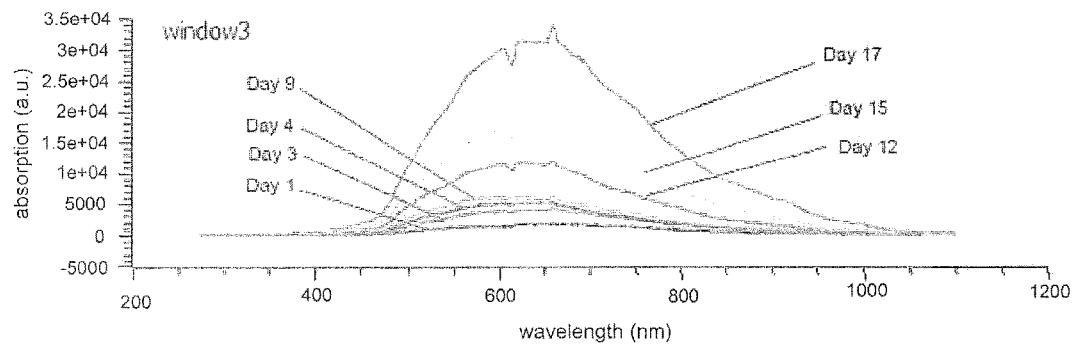
FIG. 3 depicts absorption data collected using the monitoring unit of FIG. 1, showing a difference in absorption (FIG. 3A) and normalized absorption (FIG. 3B) with biomass increase in the developed monitoring unit over time.
Figure 3B:
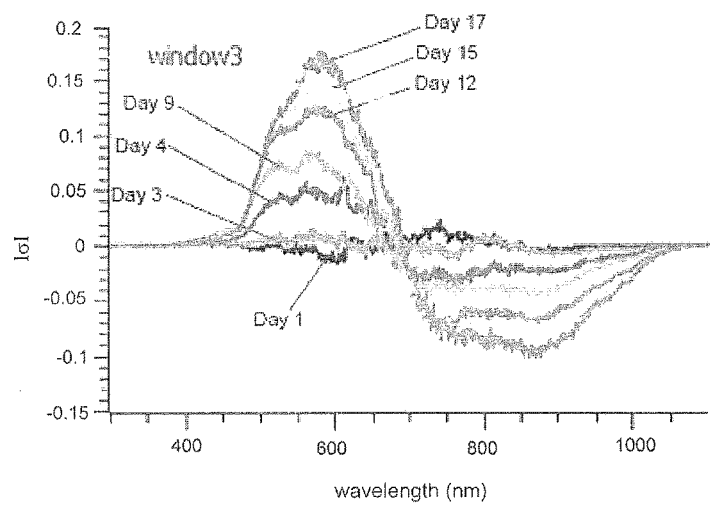

FIG. 3(a) depicts the difference in the absorption data collected. With reference to FIG. 3(b), the normalized absorption spectra at 600 nm indicates the presence of photosynthetic organism, mainly consisting of cyanobacteria. Normalized absorption at 920 nm indicates the presence of living organisms.

Figure 4:
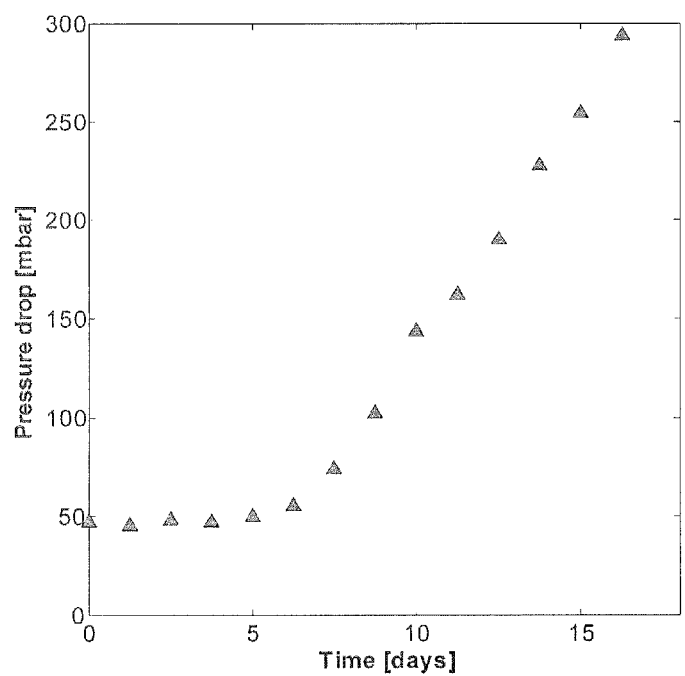
FIG. 4 depicts differential pressure data collected using the monitoring unit of FIG. 1, showing an increase in differential pressure over time due to fouling accumulation.

FIG. 4 depicts the differential pressure data collected. The increase in differential pressure over the developed monitor during the test period indicates an increase in the accumulated amount of fouling.

Fouling was thus determined by (i) the differential pressure measurements, (ii) the luminescent spectra, and (iii) the absorption spectra. After the above mentioned online measurements the monitor was opened and the presence of the indicated fouling was confirmed using visual (microscope) technics.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are included within this disclosure.

The invention claimed is:

1. A method of detecting and characterizing fouling of a component in a fluid-based system, the method comprising:
providing a monitoring unit in the system in conjunction with the component, wherein the monitoring unit comprises a test component configured to mimic fouling of the component and through which a portion of the fluid in the fluid-based system is passed;
collecting fouling data of the test component by irradiating the test component with a light source and collecting data in the form of (1) spectroscopic data from the test component and (2) a pressure difference across the test component;
determining the presence of fouling of the component from the fouling data; and
characterizing the fouling of the component from the fouling data,
wherein the spectroscopic data includes luminescent spectra and absorption spectra.

2. The method of claim 1, wherein the fluid-based system includes a fluid that is a liquid or gaseous substance containing biological, organic, inorganic or particulate matter, or any combination thereof.

3. The method of claim 1, wherein the component is a membrane, a pipe, or a reactor.

4. The method of claim 1, wherein the component is a component selected from the group consisting of microfiltration, ultrafiltration, nanofiltration, a reverse osmosis, heat exchanger, forward osmosis, osmosis, reverse electrodialysis, electro-deionisation and membrane distillation devices.

5. The method of claim 1, wherein the component is a membrane selected from the group consisting of tubular, spiral, hollow fiber, flat sheet, and capillary membranes.

6. The method of claim 1, wherein the pressure difference is measured as a difference between two or more pressure measurements and the pressure difference is measured as a pressure drop across the component, a pressure drop across the test component, a difference in pressure over time, or a combination thereof.

7. The method of claim 1, wherein the pressure difference is measured continuously or semi-continuously.

8. The method of claim 1, wherein the light source comprises infrared light and the spectroscopic data further comprises reflectance data.

9. The method of claim 1, wherein the light source comprises ultraviolet light and the spectroscopic data comprises fluorescence, luminescence, Raman, or resonance Raman data.

10. The method of claim 1, wherein characterizing the fouling of the component comprises the fouling level and the identity of the foulant.

11. The method of claim 1, wherein the fouling data further comprises a flow rate and the method further comprises measuring the flow rate.

12. The method of claim 1, wherein the foulant is selected from the group consisting of inorganic, organic, colloidal, and microbial foulants.

13. A method of detecting and characterizing fouling of a component in a fluid-based system, the method comprising:
providing a monitoring unit in the system in conjunction with the component, wherein the monitoring unit comprises a test component configured to mimic fouling of the component and through which a portion of the fluid in the fluid-based system is passed;
collecting fouling data of the test component by irradiating the test component with a light source and collecting data in the form of (1) spectroscopic data from the test component and (2) a pressure difference across the test component, the pressure difference data collected being representative of two or more time intervals;
determining the presence of fouling of the component from the fouling data; and
characterizing the fouling of the component from the fouling data corresponding to the two or more time intervals,
wherein the spectroscopic data includes luminescent spectra and absorption spectra.

14. The method of claim 13, wherein the test component comprises a test membrane, a test pipe, or a test reactor designed to mimic the fouling of the component in the fluid-based system.

15. The method of claim 13, wherein the test component is a test membrane selected from the group consisting of tubular, spiral, hollow fiber, flat sheet, and capillary membranes.

16. The method of claim 13, wherein the fluid in the fluid-based system is a liquid or gaseous substance containing biological, organic, inorganic or particulate matter, or any combination thereof.

17. The method of claim 13, wherein the component is a membrane, a pipe, or a reactor.

18. The method of claim 13, wherein the component is a component selected from the group consisting of microfiltration, ultrafiltration, nanofiltration, a reverse osmosis, heat exchanger, forward osmosis, osmosis, reverse electrodialysis, electro-deionisation and membrane distillation devices.

* * * * *